(12) United States Patent
Angelopoulos et al.

(10) Patent No.: US 11,478,164 B2
(45) Date of Patent: Oct. 25, 2022

(54) WATER AND SALT RESISTANT SOLID SUPER-ACID CATALYSTS

(71) Applicant: University of Cincinnati, Cincinnati, OH (US)

(72) Inventors: Anastasios P. Angelopoulos, Cincinnati, OH (US); Jonathan A. Bernstein, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 1334 days.

(21) Appl. No.: 15/021,308

(22) PCT Filed: Sep. 11, 2014

(86) PCT No.: PCT/US2014/055248
§ 371 (c)(1),
(2) Date: Mar. 11, 2016

(87) PCT Pub. No.: WO2015/038814
PCT Pub. Date: Mar. 19, 2015

(65) Prior Publication Data
US 2016/0220146 A1    Aug. 4, 2016

Related U.S. Application Data

(60) Provisional application No. 61/876,739, filed on Sep. 11, 2013, provisional application No. 62/018,216, filed on Jun. 27, 2014.

(51) Int. Cl.
| | | |
|---|---|---|
| *A61B 5/021* | (2006.01) | |
| *A61B 5/08* | (2006.01) | |
| *A61B 5/145* | (2006.01) | |
| *B01J 31/10* | (2006.01) | |
| *B01J 35/06* | (2006.01) | |

(Continued)

(52) U.S. Cl.
CPC .......... *A61B 5/082* (2013.01); *A61B 5/14532* (2013.01); *B01J 31/10* (2013.01);
(Continued)

(58) Field of Classification Search
CPC ...................................... A61B 5/082
See application file for complete search history.

(56) References Cited

U.S. PATENT DOCUMENTS

| | | |
|---|---|---|
| 6,465,120 B1 | 10/2002 | Akita et al. |
| 6,893,552 B1 | 5/2005 | Wang et al. |

(Continued)

OTHER PUBLICATIONS

Ayyadurai et al. "Perfluorosulfonic acid membrane catalysts for optical sensing of anhydrides in the gas phase" Anal. Chem. 2010, 82, 14, 6265-6272, Jun. 18, 2010 (Year: 2010).*

(Continued)

*Primary Examiner* — Allen Porter
*Assistant Examiner* — Michael A Catina
(74) *Attorney, Agent, or Firm* — Dinsmore & Shohl LLP

(57) ABSTRACT

Methods for preserving catalytic activity of a PSA polymer membrane in a humid environment by immobilizing in the membrane an organic acid having a pKa greater than the pKa of the PSA polymer membrane; optical sensors based on the PSA membranes further including an immobilized organic reagent capable of reacting with a target compound in a humid environment to produce a detectable color shifted product; and non-invasive methods for estimating blood glucose concentration by utilizing an optical sensor to detect concentration of acetone in exhaled human breath and correlating it to blood glucose concentration.

10 Claims, 10 Drawing Sheets

(51) Int. Cl.
*B01J 37/02* (2006.01)
*G01N 21/78* (2006.01)
*G01N 33/64* (2006.01)
*G01N 33/497* (2006.01)
*G01N 21/75* (2006.01)

(52) U.S. Cl.
CPC ......... *B01J 35/065* (2013.01); *B01J 37/0203* (2013.01); *G01N 21/783* (2013.01); *G01N 33/64* (2013.01); *G01N 2021/757* (2013.01); *G01N 2033/4975* (2013.01)

(56) References Cited

U.S. PATENT DOCUMENTS

| | | | |
|---|---|---|---|
| 6,936,365 B2* | 8/2005 | Hobson | C08J 5/2287 |
| | | | 429/494 |
| 7,538,169 B2 | 5/2009 | Hobson et al. | |
| 2009/0081427 A1 | 3/2009 | Kuruma | |
| 2011/0160319 A1 | 6/2011 | Tsai et al. | |

OTHER PUBLICATIONS

Chuji Wang et al., "A Study on Breath Acetone in Diabetic Patients Using a Cavity Ringdown Breath Analyzer Exploring Correlations of Breath Acetone with Blood Glucose and Glycohemoglobin A1C"; IEEE Sensors Journal, vol. 10, No. 1, Jan. 2010, pp. 54-63.

Adam D. Worrall et al., "Portable Method of Measuring Gaseous Acetone Concentrations"; Talanta 112 (2013) 26-30.

* cited by examiner

Note: The error bars show +/- one standard deviation from the data collected.

Table 1. Subject Characteristics

| Subject | Gender | Age, yr | Blood Glucose, mg/dL |
|---|---|---|---|
| Diabetic 1 | F | 73 | 161 |
| Diabetic 2 | M | 55 | 116 |
| Diabetic 3 | M | 63 | 117 |
| Diabetic 4 | F | 68 | 191 |
| Diabetic 5 | M | 55 | 163 |
| Diabetic 6 | F | 67 | 112 |
| Diabetic 7 | F | 80 | 134 |
| Diabetic 8 | F | 70 | 118 |
| Diabetic 9 | F | 54 | 201 |
| Diabetic 10 | F | 40 | 144 |
| Diabetic 11 | F | 22 | 115 |
| Diabetic 12 | M | 56 | 95 |
| Diabetic 13 | F | 41 | 128 |
| Mean ± SD | | 57 ± 16 | 138 ± 32 |
| Control 1 | F | 27 | 107 |
| Control 2 | F | 24 | 108 |
| Control 3 | F | 45 | 99 |
| Control 4 | F | 65 | 141 |
| Control 5 | M | 65 | 107 |
| Control 6 | F | 72 | 104 |
| Mean ± SD | | 50 ± 21 | 111 ± 15 |

Figure 8

TABLE 2

| Acid | pKa in Water at 20°C | Imbibing Solvent | Solution Concentration (M) | Membrane Concentration (M) | Absorbance at 400nm from Exposure to 4ppmv Acetone at 100% RH |
|---|---|---|---|---|---|
| Perfluorosulfonic Acid | -14 | - | - | - | - |
| Benzoic Acid | 4.20 | Mineral Oil | 0.049 | - | 0.041 |
|  |  |  | 0.205 | - | 0.078 |
| Vanillic Acid | 4.50 | 3:1 Mineral Oil : Ethyl Acetate | 0.016 | 0.025 | 0.014 |
|  |  |  | 0.040 | 0.054 | 0.023 |
|  |  |  | 0.074 | 0.076 | 0.083 |
| Ferulic Acid | 4.58 | Mineral Oil | 0.031 | - | 0.000 |
|  |  |  | 0.129 | - | 0.179 |
| Tiglic Acid | 4.96 | Mineral Oil | 0.063 | 0.062 | 0.122 |
|  |  |  | 0.257 | 0.115 | 0.172 |
|  |  |  | 0.502 | 0.179 | 0.345 |
|  |  |  | 1.501 | 0.502 | 1.014 |

WATER AND SALT RESISTANT SOLID SUPER-ACID CATALYSTS

PRIORITY

The present application claims priority under 35 U.S.C. § 119(e) to U.S. Provisional Application Ser. Nos. 61/876,739 filed Sep. 11, 2013, and 62/018,216 filed Jun. 27, 2014.

BACKGROUND

Sulfonated and perfluorosulfonic acid (PSA) polymers, such as the commercially available compounds Amberlyst® and Nafion®, respectively, have been of long-standing interest as sustainable solid acid catalyst alternatives to toxic, non-reusable homogeneous acid catalysts in the production of high-volume specialty chemicals such as methyl tert-butyl ether (MTBE) and Bisphenol-A. As the demand for portable energy increases, these materials are also attracting renewed attention as heterogeneous biodiesel synthesis catalysts in place of homogenous alkali for renewable energy applications. These materials eliminate the extensive work-up procedures required to introduce acidity into more typical zeolite and mixed metal oxide catalysts, yet retain the advantage of clean product separation afforded by heterogeneous catalysts. In addition, these materials have exhibited significant activity in the presence of fatty acid impurities, which are common in low-cost vegetable oil feedstock. PSA polymer catalysts can be used a broad range of technologically important organic synthesis reactions.

The present investigators recently demonstrated that PSA polymer membranes can be used as both solid acid catalysts and durable scaffold materials in the preparation of optical sensors. Earlier work resulted in the discovery that by immobilizing a dihydroxy-benzene reagent, into a PSA polymer membrane; a controlled organic synthesis occurs and a selective product of this reaction (e.g., a flavan in the case of acetone and various quinones in the case of anhydrides) is found to produce a visible spectrum color change which could be employed to measure target molecule concentrations to less than parts per billion (ppb). This approach was utilized to develop portable optical sensing devices for real-time, non-invasive analyses in medical diagnostics, occupational settings, and environmental testing.

A key drawback, however, to the use of solid acid polymers as catalysts is that they can be readily deactivated by the presence of water as well as salt impurities present in the environment. Without being bound by theory, it is believed that cations such as $K^+$ and $Ca^{++}$ can exchange with protons in the polymer and reduce or ultimately eliminate polymer acidity. The same super-acidic nature that makes these materials highly active catalysts also results in their ready de-protonation by salts. Furthermore, water incorporation can dilute local acidity within the membrane. For example, an ambient relative humidity less than 15% has been found sufficient to completely deactivate an 1100 Equivalent Weight sample of Nafion for acetone condensation with resorcinol in an optical sensing device of the prior art. Furthermore, not only catalyst de-activation but proton conductivity may be completely disrupted due to cation exchange of protons with impurities such as $K^+$ and $Ca^{++}$ present in the environment. Such behavior has limited the use of PSA polymer catalysts to toxic and flammable organic solvents or to high temperatures, and has also prevented commercial realization in real environments of the previously developed optical sensing elements for portable, real time gas analysis. In particular, exhaled breath for medical diagnostic purposes has relative humidity levels that approach 100% and a method has yet to be developed to provide accurate real-time trace gas analyses in such an environment. Further, although detection and measurement of formaldehyde concentrations in dry environments is possible, it would be desirable to test for presence and amount of formaldehyde in humid environments, such as in fuel cell effluent where concentration is a measure of efficiency loss in the fuel cell.

Hence, there remains a need in the art for PSA polymer catalysts capable of retaining catalytic activity in humid environments. Further, there is a need in the art for portable non-invasive optical sensors capable of reliably measuring concentration of volatile organic compounds in high-humidity and/or high-salt environments associated with medical diagnostics and fuel cell efficiency determinations.

SUMMARY

Accordingly, one broad embodiment of the invention provides PSA polymer membranes reformulated to maintain their catalytic activity even in high-humidity and potentially high-salt environments. Further embodiments provide optical sensing devices comprising certain inventive PSA membranes designed to produce a color-shift reaction product in the presence of target compounds in humid environments. Specific clinical and environmental applications of optical sensing device according to the invention designed to detect, for example, acetone in exhaled human breath and formaldehyde in fuel cell effluent are also described.

In particular, an embodiment directed to a method of preserving the catalytic activity of a solid sulfonic acid catalyst polymer in a humid environment is provided. Broadly characterized the method comprises immobilizing an organic acid in the solid sulfonic acid catalyst polymer, wherein the pKa of the immobilized acid is greater than the pKa of the solid sulfonic acid catalyst polymer.

Another embodiment provides optical sensors for detecting target compounds in a humid environment. The optical sensor comprises a PSA polymer catalyst membrane comprising an immobilized organic acid having a pKa greater than the pKa of the PSA polymer membrane, and an immobilized organic reagent. The organic reagent is capable of reacting with the target compound to produce a color shifted product such that exposure of the optical sensor to the target compound in a humid environment produces a detectable color shift on the optical sensor. The optical sensor may be fabricated into a portable optical sensing device. Specific embodiments with utility in medical diagnostics, detection of environmental contamination, and analysis of fuel cell efficiency are disclosed.

A further embodiment provides a real-time non-invasive method for estimating blood glucose concentration in a human based on a calculated concentration of acetone in exhaled breath of the human in accordance with particular aspects of the invention. The method comprises: providing a PSA membrane comprising immobilized organic reagent and at least one immobilized organic acid having a pKa greater than the pKa of the PSA polymer membrane, the immobilized reagent selected such that a reaction occurs between the organic reagent and acetone to produce a detectable color-shifted product; exposing the PSA polymer membrane to a volume of exhaled breath; measuring concentration of a product of the reaction based on a detected color shift; calculating the concentration of acetone in the volume of exhaled breath from the concentration of product measured; and correlating the concentration of acetone to a standard blood glucose concentration. The inventive methods, sensors and membranes may be used as part of a treatment regimen for diabetic patients in the monitoring of blood glucose levels in the patient across a time frame and adjusting the patient's insulin levels accordingly.

These and other aspects and embodiments are described more clearly and will be further understood by reference to the Detailed Description. Figures and Examples are provided herein to illustrate particular aspects and features of embodiments of the invention, and should not be construed as limiting of the scope of the invention as defined by the instant claims.

All references (e.g., printed publications such as books, papers, patents, patent applications, catalogs, databases) are incorporated herein by reference. In the event of a conflict or inconsistency, the present specification, as modified by any amendments thereto, shall control.

BRIEF DESCRIPTION OF THE FIGURES

FIG. 8. Table 1. Sets forth patient characteristics and blood glucose concentrations for patients in exhaled breath study.

FIG. 9. Table 2. Sets forth compiled data derived from investigation of a variety of possible organic acid additives suitable in resorcinol-imbibed PFSA catalytic membranes.

Figure 10:
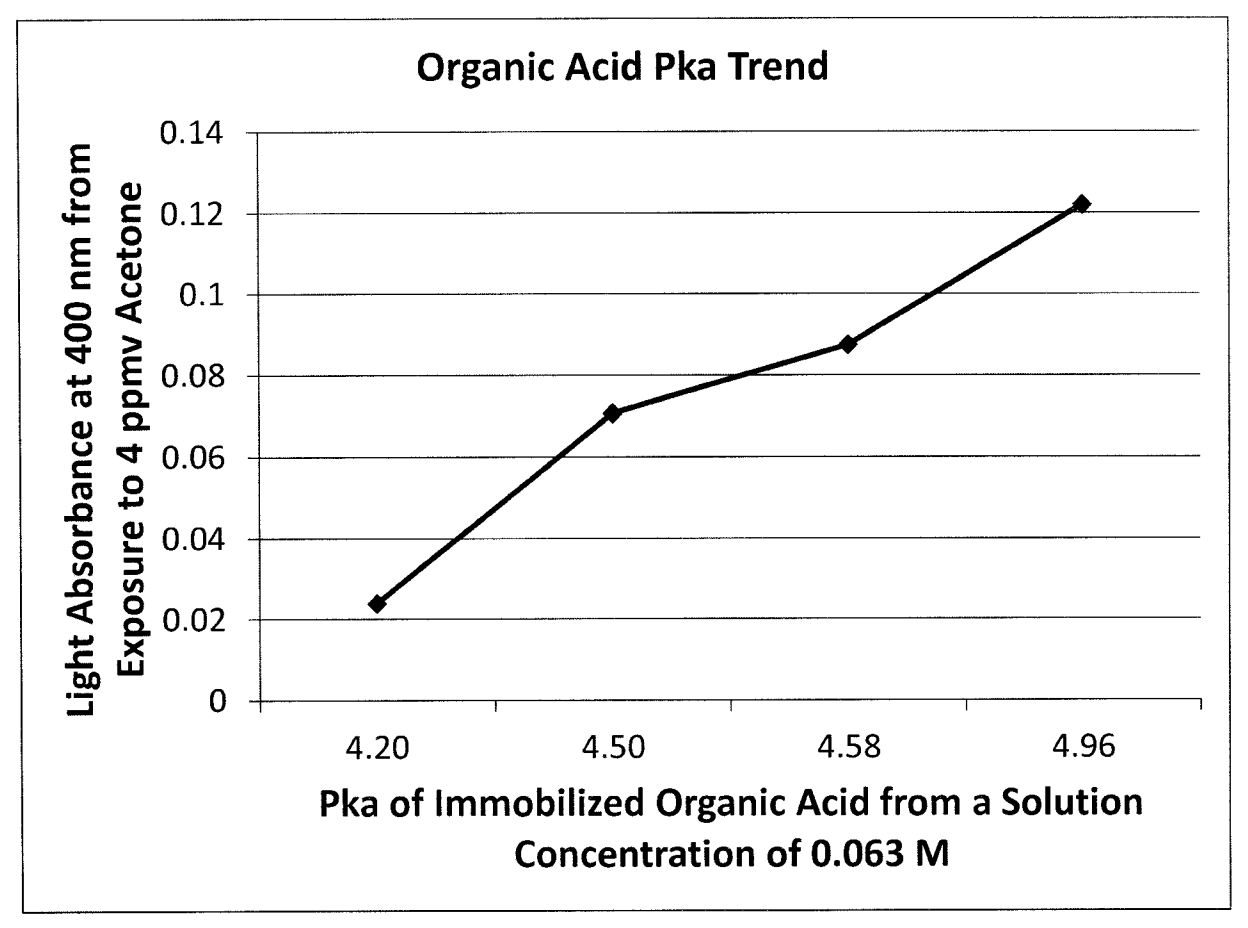

FIG. 10. Depicts organic acid pKa trend for purposes of optimizing selection of organic acid additive in resorcinol-imbibed PFSA catalytic membranes. Trend is based on interpolation of data from Table 2 at 0.063 M solution concentration.

DETAILED DESCRIPTION

Figure 1:
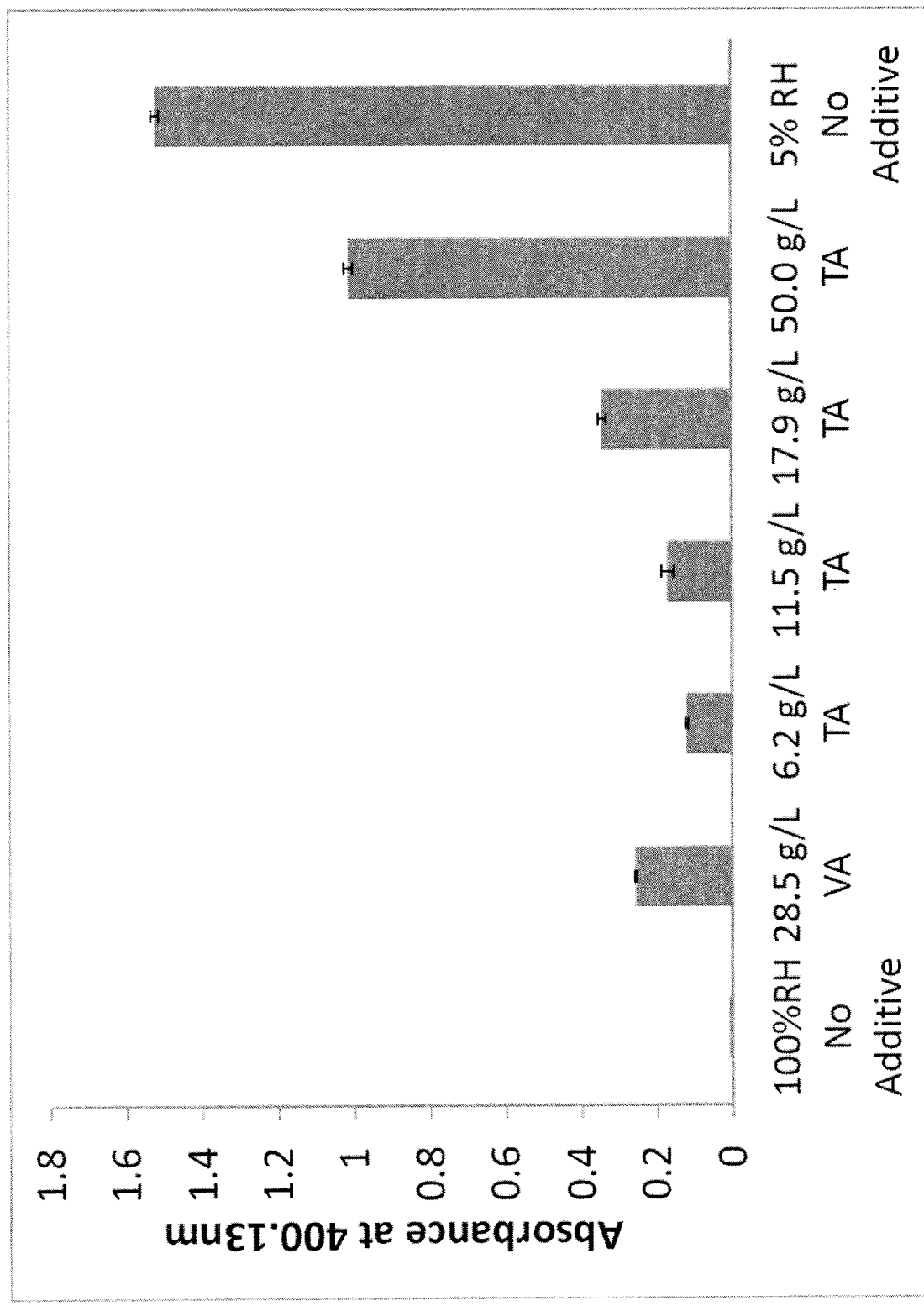
FIG. 1. Compares absorbance of PSA membrane comprising immobilized resorcinol with VA additive and TA additive at varying concentrations, and absorbance of control membranes without additive under low and high humidity conditions.

The present investigators have developed PSA catalytic polymer membranes, and methods and devices employing them, that overcome deficiencies in the art relating to loss of catalytic activity in humid environments. The inventive PSA catalytic polymer membranes surprisingly exhibit retention of catalytic activity in high-humidity and high-salt environments by immobilization of proton donating compounds such as organic acids within the hydrophilic cluster network of the PSA polymers. The organic acid components are selected to increase the pKa of the PSA in a manner analogous to mixed solvent effects in homogeneous liquid-phase systems. However, the phenomenon has not been previously observed in high molecular weight, heterogeneous-phase systems.

The fundamental principal behind the solution rests in choosing proton-donating compounds with a proton affinity (PA) that is greater than that of the PSA groups subsequent to immobilization within the hydrophilic polymer cluster network. Energetically, the following requirement must be fulfilled:

$$PA(AH^*) - PA(PSA) > 0 \qquad \text{Eq. (1)}$$

Where PA(Y) is the proton affinity of the respective compound Y and AH* is the immobilized form of the proton-donating compound AH within the PSA cluster network. Suitable exemplary compounds AH that have been identified as fulfilling this criterion in the case of 1100 equivalent weight Nafion® include vanillic acid, tiglic acid and ferulic acid (see e.g. Table 2/FIG. 9). Extensions to identification of other effective compounds may be readily made in light equation (1). Although identification of effective compounds is relatively simple, empirical validation is needed to assess suitability for a particular reagent-imbibed PSA catalytic membrane and contemplated detectable synthetic reaction. FIG. 10 illustrates a pKa trend graph for a very particular embodiment of a resorcinol-imbibed PSA catalytic membrane compiled from the data set forth in Table 2 (FIG. 9) and illustrates the principle for selection optimization of the organic acid additive.

PSA polymer catalysts may be reformulated so as to maintain their catalytic activity even in such high-humidity and potentially high-salt environments. Embodiments of the invention provide methods of preserving the catalytic activity of a solid sulfonic acid catalyst polymer in a humid environment, and unique PSA polymer membranes that exhibit retention of catalytic activity in high-humidity and high-salt environments. Particular method embodiments comprise immobilizing an organic acid in the solid sulfonic acid catalyst polymer. The organic acid additive is selected such that the pKa of the immobilized acid is greater than the pKa of the solid sulfonic acid catalyst polymer. In specific embodiments the polymer is a PSA polymer membrane and in more specific embodiments the membrane is a dihroxy benzene imbibed PSA membrane. According to very specific embodiments the membrane is a resorcinol imbibed PSA polymer membrane. Highly specific embodiments include resorcinol imbibed Nafion® PSA membranes comprising immobilized additive.

The utility of PSA polymer catalysts in organic synthesis is well-known. A number of such reactions is set disclosed in Olah et al "Perfluorinated Resinsulfonic Acid (Nafion-H®) Catalysis in Synthesis" Synthesis July 1986 pp 513-531, the entire disclosure of which is incorporated herein by this reference. Non-limiting examples of synthetic reactions which may be benefited by the instant invention include Alkylation and acylation of aromatics with olefins, alcohols, allyl halides, and alkyl esters, condensation with ketones (illustrated herein with acetone), and aldehydes (illustrated herein with formaldehyde), oligomerization of olefins, Isomerization, transalkylation, and disproportionation of alkyl benzenes, nitration of aromatics, sulfonation, phosphorylation, and ether/ester synthesis. Although these are disparate reactions, the instant invention relates specifically to retention of catalytic activity of the PSA polymer catalysis, which is the commonality. Hence, although the instant disclosure illustrates and validates the inventive principle with specific synthetic reactions, the methods for retention of catalytic activity in humid environments is generalizable.

An organic acid additive that demonstrates the selection criterion with respect to pKa relative to the membrane is readily determinable by a person of ordinary skill in the art, and is dependent upon the desired end-use of the membrane and the specific membrane property profile. For example, for embodiments involving catalysis of a resorcinol dye color-shifting reaction by a PSA membrane, small organic acid additives are particularly suitable. Non-limiting examples include benzoic, vanillic, tiglic and ferulic acid. In specific embodiments the acid additive comprises vanillic or tiglic acid, and in very specific embodiments the acid comprises tiglic acid. The additive may be immobilized in the membrane by soaking in an imbibing solvent and suitability may vary with characteristics of the acid and the membrane. An exemplary imbibing solvent for small organic acid additive in a PFSA membrane comprising immobilized dihydroxy-benzene reagent comprises a mineral oil composition. The imbibing composition comprises mineral oil and solubility-adjusting agents such as ethanol or ethyl acetate where needed.

The optical sensing technique according to embodiments of the invention utilizes ultraviolet/visible light spectrophotometry. This method detects changes in absorption of ultraviolet or visible light within a medium due to the presence of a chemical compound of interest. A Nafion® membrane, also referred to as a perfluorosulfonic acid (PSA) membrane, is used as the medium. The PSA membrane is a copolymer membrane consisting of dispersed hydrophilic PSA regions within a hydrophobic tetrafluoroethylene matrix. Because of this morphology, it has transport properties that allow movement of cations and the immobilization of many dye molecules such as resorcinol. In addition, the hydrophilic PSA regions can act as acid catalysts. Consequently, in the presence of different volatile organic compounds, such as formaldehyde and acetone, the immobilized resorcinol will react, producing a color change, providing a visible detection of these compounds.

I. Illustration and application of the principle to development of an optical sensor for detection of acetone in exhaled human breath.

There has been a growing interest in the medical community for non-invasive medical testing techniques for the detection of volatile organic compounds (VOCs) in human breath. Chemicals such as nitrous oxide and acetone can be used to help detect and diagnose lung cancer and diabetes mellitus respectively. Acetone is produced by the liver as it breaks down fat molecules. In patients with diabetes mellitus, this process results in the production of ketone bodies which are further metabolized to acetone. The acetone is then excreted through urine as well as exhaled breath. Diabetics excrete acetone breath concentrations well in excess of that of a healthy individual (usually 1 to 4 parts per million by volume (ppmv) compared to the 0 to 0.5 ppmv seen in healthy individuals). These breath concentrations can be correlated with blood glucose concentrations in diabetics to monitor the patient's condition allowing for better control over the symptoms than provided by blood glucose measurements alone.

While there are many breath analysis methods available for the detection of acetone and other VOCs, methods such as cavity ringdown spectroscopy and selected ion flow tube mass spectroscopy are expensive and require laboratory support. There has been a recent push for portable detection technologies that provide accurate VOC detection such as resistance based nanomaterials, conductive polymer nanocomposites, and colorimetric response systems. However, these techniques are currently limited in part due to interferences from the presence of water vapor. In optical and electrical sensing techniques, water vapor can provide false positives by reacting with the detection media thus lowering the selectivity of the sensor, deactivating the catalyst used in the process, or reducing the sensitivity of response in the sensor, which greatly decreases the accuracy and precision necessary to be utilized in a medical device.

Capability of detecting acetone in low concentrations in dry air samples utilizing the acid catalyzed condensation reaction of acetone with resorcinol has previously been demonstrated. This technique was developed by the present investigators using a PSA membrane, in this case Nafion® 1100, as the acid catalyst for the reaction and the technique was shown to provide a highly sensitive, rapid, and selective colorimetric response with acetone.

According to embodiments of the invention, the addition of immobilized organic acids into the ionic clusters of PSA membranes is used in heterogeneous gas-solid systems to successfully mitigate the interference of water in the detection of acetone. By immobilizing various organic acids within the ionic clusters of the membrane, it is possible to lower the effective pKa of the sulfonic acid groups within the clusters and maintain the acid catalyst activity. The solution is novel both with respect to mitigation of water interference in a chemical sensing device as well as the utilization of a weak acid to lower the pKa of a strong acid in a heterogeneous system.

Loss of catalytic activity in a Nafion® PFSA membrane in the presence of high humidity is believed to occur due to introduction of significant concentrations of water vapor in the ionic clusters that impede the reaction by diluting the acidity of the sulfonic groups due to the highly rapid dissociation of the sulfonic acid groups within the cluster. As the reaction of acetone and resorcinol can occur using other strong acids in aqueous environments, it is clearly a problem with the membrane support. The present investigators confirmed this hypothesis by employing several weak organic acids to shift the pKa of the sulfonic acid groups enough to lower the dissociation rate but not enough to significantly alter the catalytic activity of the ionic clusters as detailed above.

FIG. 1 shows a comparison of vanillic acid and several concentrations of tiglic acid used on PSA membranes containing resorcinol exposed to 4 ppmv acetone in the presence of 100% relative humidity (RH). The concentration values are for the amount of the organic acid observed in the membrane, which was determined by conducting a series of extractions from the membrane to determine the partition coefficient of the acids with the PSA membrane. For comparison, the absorbance value for membranes without the presence of an organic acid additive in ambient humidity (which at 60° C. is reduced to ~5% RH) and 100% RH are included. It was found that in the presence of high concentrations of tiglic acid the water interference was significantly reduced allowing for a strong signal response at 100% RH. The addition of vanillic acid did not have as significant an effect on signal response even at the membrane saturation concentration. This is possibly due to the difference in acid strength for the two acids, as vanillic acid has a pKa of 4.50 and tiglic acid has a pKa of 4.96 in water at 25° C. With a higher pKa, tiglic acid would allow the sulfonic acid groups to retain more acidity than the vanillic acid.

Figure 2:
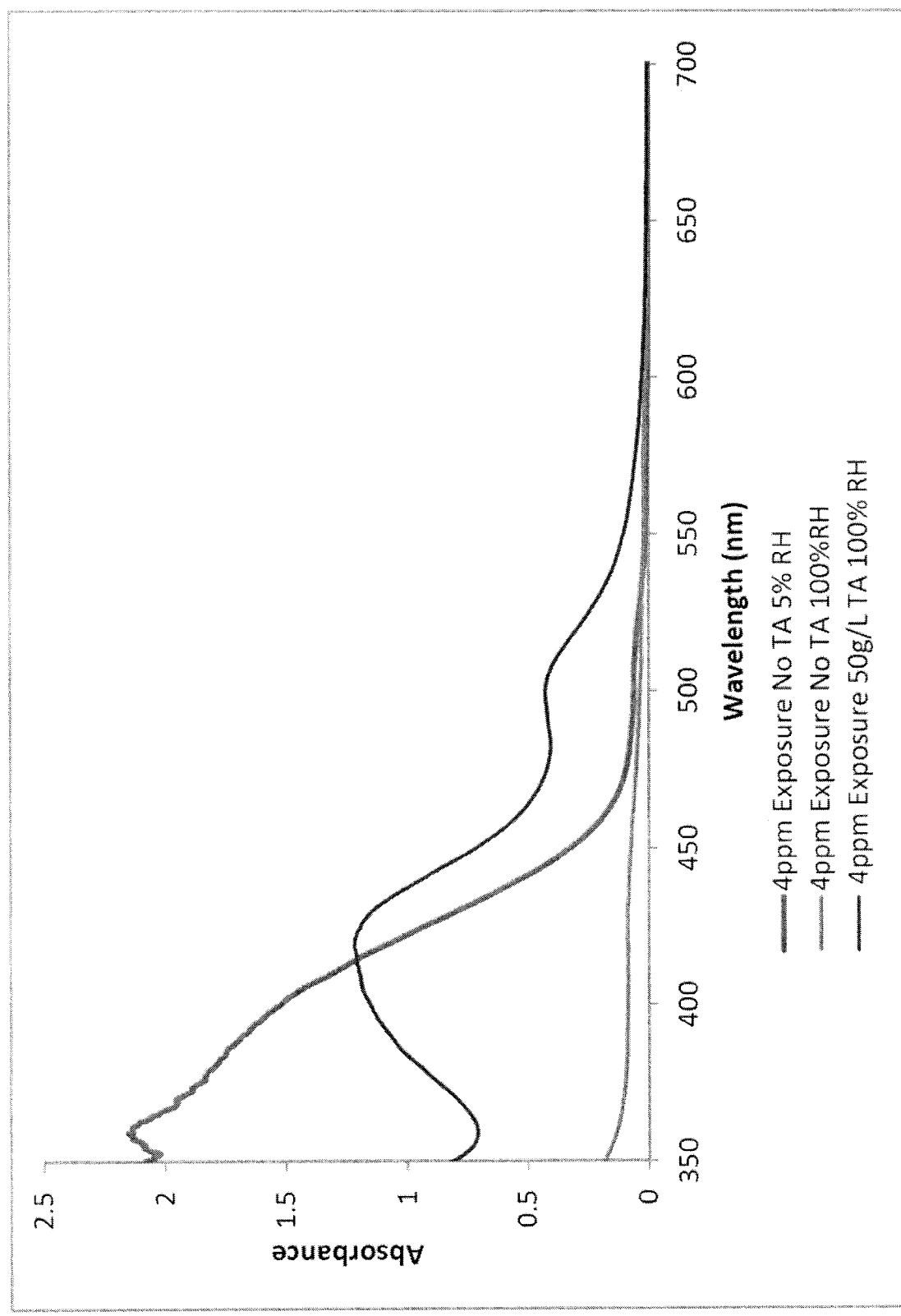
FIG. 2. Depicts absorption spectra of PSA membrane comprising immobilized resorcinol with and without TA additive in low and high relative humidity.

In addition, tiglic acid features a strong resonance structure which would allow for stronger H-bonding within the ionic cluster further protecting the sulfonic acid groups from rapid dissociation in the presence of water. FIG. 2 shows spectra from sample membranes used to produce FIG. 1. From the plot it is clear that the addition of tiglic acid produces a significant bathochromatic shift due to the change in the local environment in the ionic clusters of the membrane.

The possibility that the organic acid absorbed was simply limiting water uptake into the membrane was tested and excluded. A series of water uptake studies were conducted using a microbalance as detailed above. The control data consisting of a group of untreated membranes were found to increase in mass by 19.02% (±0.61%) while the membranes treated with tiglic acid showed an increase in mass of 17.31% (±3.15%). It is clear that there was no significant reduction in water uptake due to the presence of tiglic acid indicating that water was not being excluded from the membrane but was mitigated by another means.

Figure 3:
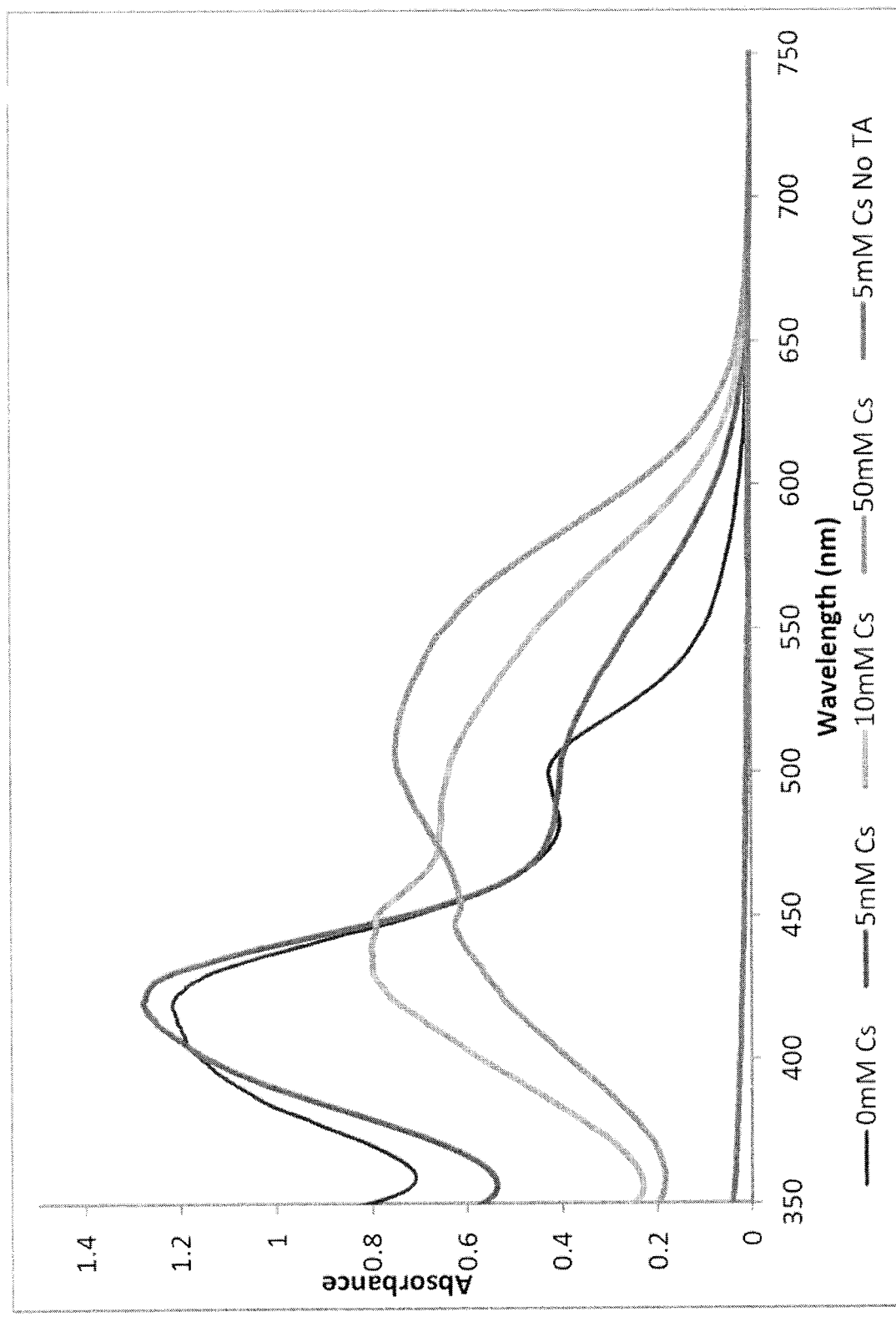
FIG. 3. Depicts absorption spectra of PSA membrane comprising immobilized resorcinol and TA additive in the presence of acetone, water, and cesium and the effect of cesium concentration on the performance of the TA additive in retention of catalytic activity.

To probe what was happening inside of the ionic clusters of the membrane during the reaction, varying concentrations of cesium chloride were introduced into the membranes. Cesium has been found to rapidly replace the protons on sulfonic acid groups at low concentrations resulting in a reduction in ionic transport and loss of catalytic activity in PFSA membranes. FIG. 3 shows the effects of cesium uptake on membranes exposed to 4 ppmv acetone with and without 50.0 g/L tiglic acid. Without the tiglic acid, the reaction does not occur due to the replacement of the H+ ions, but with the tiglic acid present the membranes show significant resistance to the Cs+ ions allowing for a signal response over a range of cesium concentrations. This indicates that the tiglic acid is actively protecting the sulfonic acid groups allowing for the condensation reaction to occur even in the presence of significant interferences.

Figure 4:
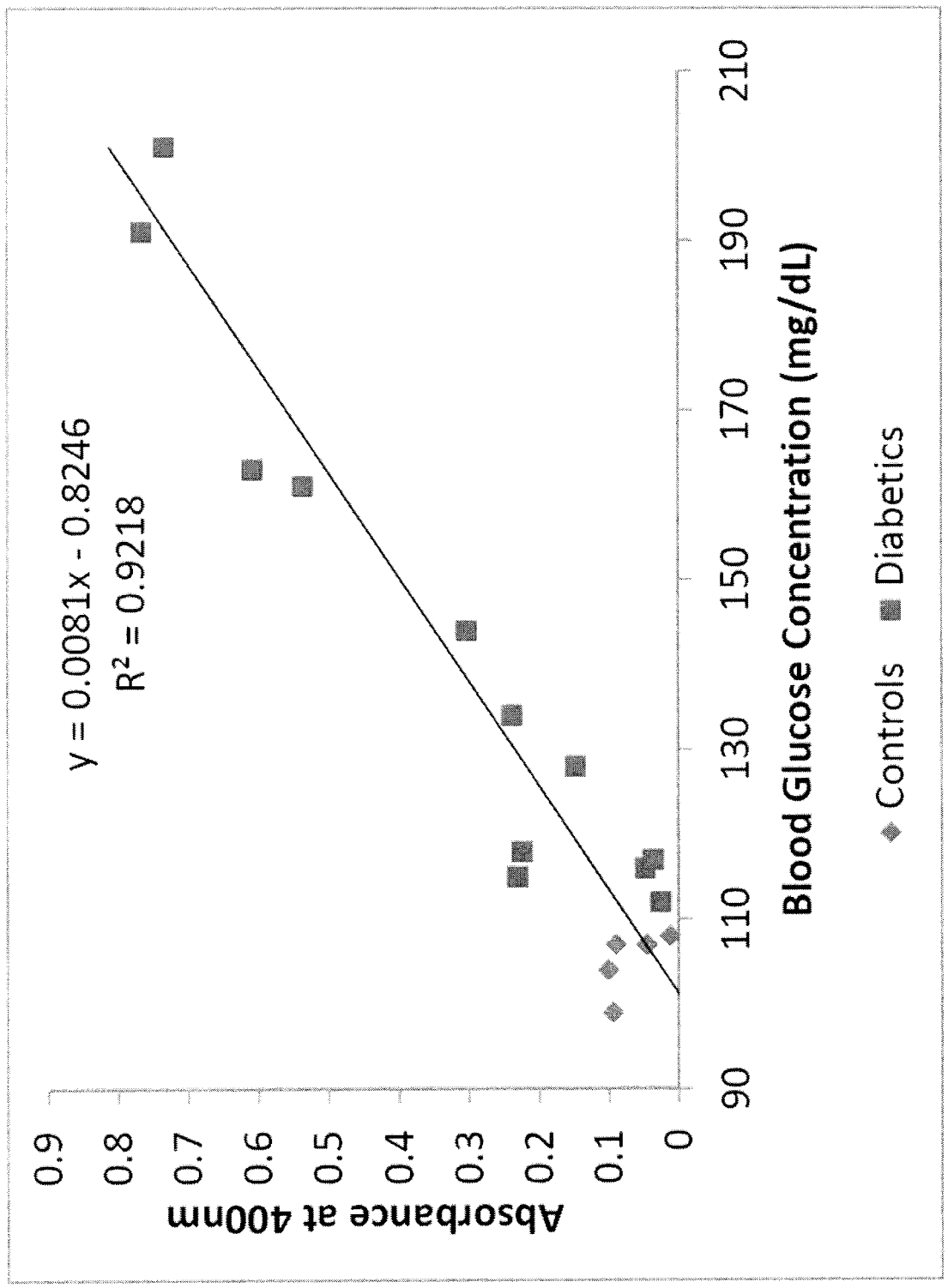
FIG. 4. Illustrates correlation between exhaled breath acetone concentration as measured by a resorcinol and TA imbibed PSA membrane-based optical sensor and simultaneously measured blood glucose concentration.

The technique is illustrated by application to evaluating whether acetone concentrations in human exhaled breath samples could be correlated with blood glucose measurements in Type 2 diabetic patients as described in Example 4. FIG. 8 sets forth Table 1 showing the characteristics for both diabetic and control patients. FIG. 4 shows the plot of the observed absorbance due to the reaction of acetone and resorcinol versus the blood glucose concentration of the subject. There was a strong linear correlation present ($R^2$=0.9218) for the samples taken indicating that it is possible to detect acetone concentrations in diabetic breath samples and it may be possible to use this technique as a non-invasive alternative to the current glucometers.

According to certain embodiments of the invention, an optical sensor capable of detecting a volatile organic compound in exhaled human breath is provided. According to specific embodiments, the target volatile organic compound comprises acetone and the PSA membrane (which may be a PFSA polymer membrane such as Nafion® PFSA catalyst membrane) comprises immobilized organic reagent that reacts with acetone to produce a detectable color-shifted product. For example the organic reagent may comprise a dihydroxybenzene such as resorcinol, which undergoes a condensation reaction with acetone, a reaction catalyzed by the PSA catalyst polymer. The immobilized organic acid is any organic acid possessing a pKa greater than the pKa of the PSA polymer membrane. In very specific embodiments the immobilized organic acid is selected from vanillic acid, benzoic acid, ferulic acid and tiglic acid, and in more specific embodiments the immobilized organic acid is tiglic acid. The optical sensor may be fabricated into an optical sensing device, and is particularly suitable for a portable optical sensing device, such as a handheld device. As depicted in FIG. 4 and detailed in Example 4, the concentration of acetone in exhaled breath of a patient correlates to blood glucose concentration in the patient, providing a simple, easy to use, non-invasive method for monitoring blood glucose levels in the patient.

Specific embodiments of the invention are directed to a real-time non-invasive method for estimating blood glucose concentration in a patient based on a calculated concentration of acetone in exhaled breath of the human. The method comprises: providing a PSA membrane comprising immobilized organic reagent and at least one immobilized organic acid having a pKa greater than the pKa of the PSA polymer membrane, the immobilized reagent selected such that a reaction occurs between the organic reagent and acetone to produce a detectable color-shifted product; exposing the PSA polymer membrane to a volume of exhaled breath; measuring concentration of a product of the reaction based on a detected color shift; calculating the concentration of acetone in the volume of exhaled breath from the concentration of product measured; and correlating the concentration of acetone to a standard blood glucose concentration. The standard blood glucose concentration may be an external standard based on a function of exhaled breath acetone concentration versus blood glucose concentration derived from a population of diabetic humans or it may be derived as an internal standard based on a function of exhaled breath acetone concentration versus blood glucose concentration longitudinally across a time frame from the human. In very specific embodiments the membrane comprises a PFSA membrane. Diabetic patients may employ the specific methods and optical sensors or portable optical sensing devices to monitor blood glucose levels across a time frame, and to adjust insulin levels accordingly.

II. Illustration and application of the principle to development of an optical sensor for detection of formaldehyde in exhaled human breath.

Formaldehyde is a volatile organic compound made by the oxidation of methanol. The US National toxicology Program recognizes formaldehyde as a carcinogen. It is also a compound used in the manufacturing of many household products, such as cleaning solutions, cosmetics, and wood fixatives (Sun et al. 2007). Formaldehyde is also a byproduct of alcohol fuel cells, which convert chemical energy into electricity through an oxidation-reduction reaction. The production of aldehydes from alcohol fuel cells is a symptom of inefficiency of the cell, as well as a contaminant in the environment.

The presence of formaldehyde in the effluent of a direct alcohol fuel cell has been previously shown to indicate efficiency loss in the fuel cell energy process. Formaldehyde is also recognized as a carcinogen and therefore is a hazardous air pollutant that raises public health concerns. It is known that immobilized resorcinol dye molecules in a perfluorosulfonic acid membrane react with gaseous formaldehyde, and that the product of this reaction produces a color change seen in the visible spectrum of light, providing a detection method for formaldehyde. The present investigators previously developed an optical sensor based on this mechanism; however the application of the sensor is limited because the reaction fails to occur in the presence of water.

Based on the same principles as enunciated in detail with respect to detection of acetone in exhaled human breath, PSA catalyst polymer membranes may be reformulated to detect formaldehyde in humid environments. Specific embodiments of the invention provide methods for mitigation of the observed water interference by retention of the PSA polymer membrane catalytic activity in the presence of water. According to very specific embodiments, optical sensing devices comprising embodiments of the inventive PSA polymer membrane allow for the detection of formaldehyde in a water-abundant environment of direct alcohol fuel cell effluent.

Figure 5:
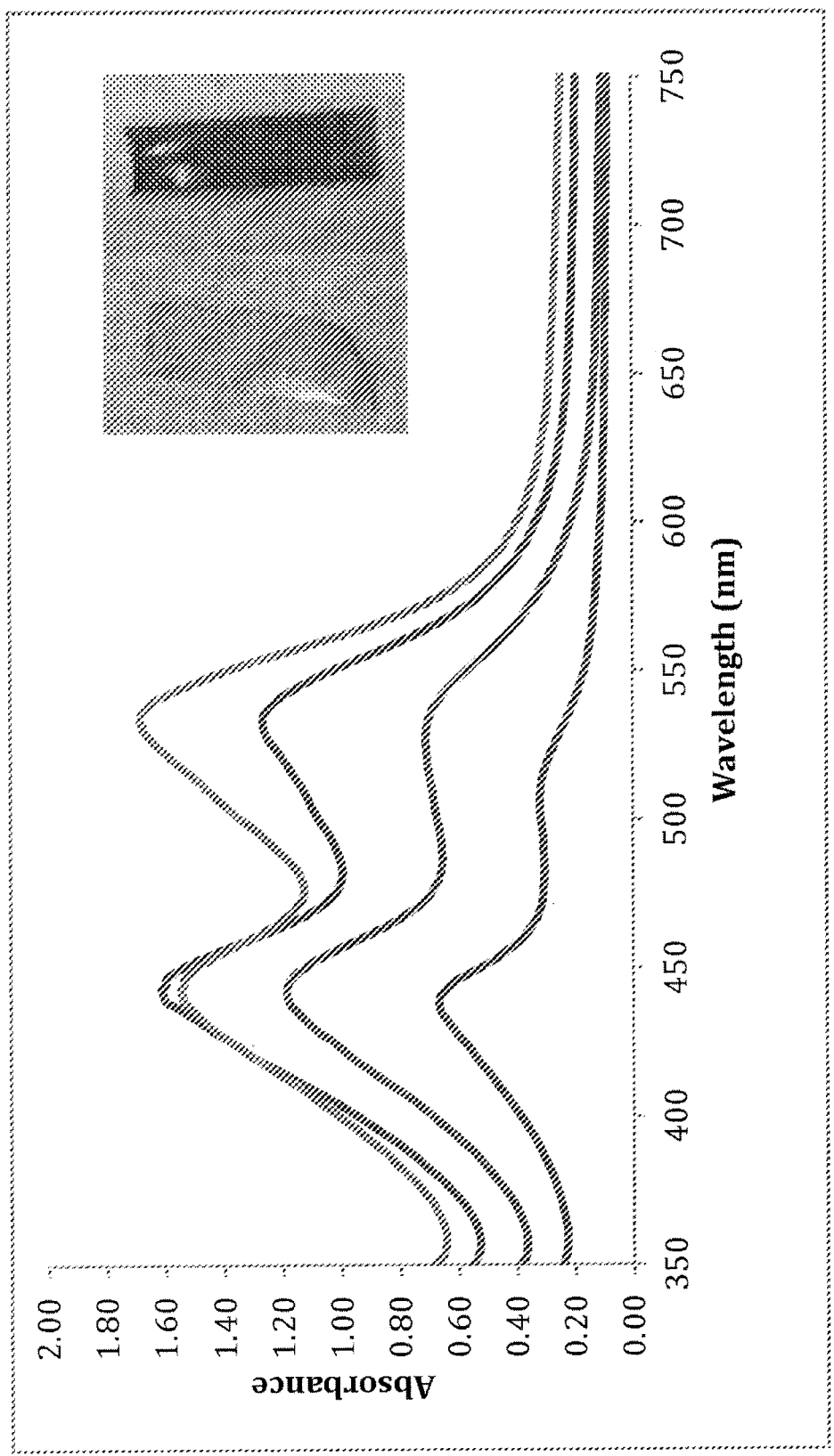
FIG. 5. Depicts absorption spectra of PSA membrane comprising immobilized resorcinol and TA additive versus formaldehyde concentration at 100% RH.
Figure 6:
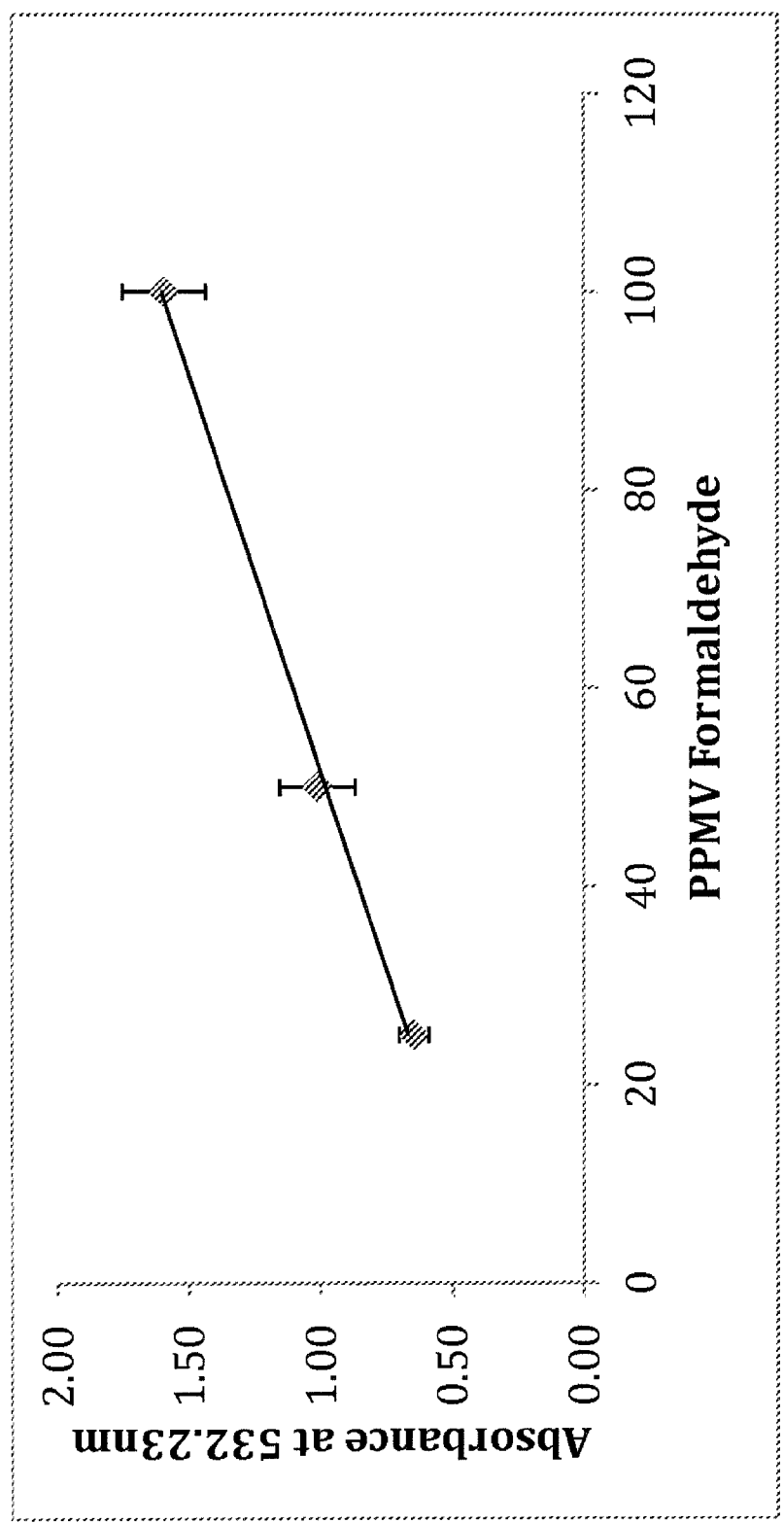
FIG. 6. Illustrates correlation between absorbance spectra of PSA membrane comprising immobilized resorcinol with additive and concentration of formaldehyde in a humid environment.
Figure 7:
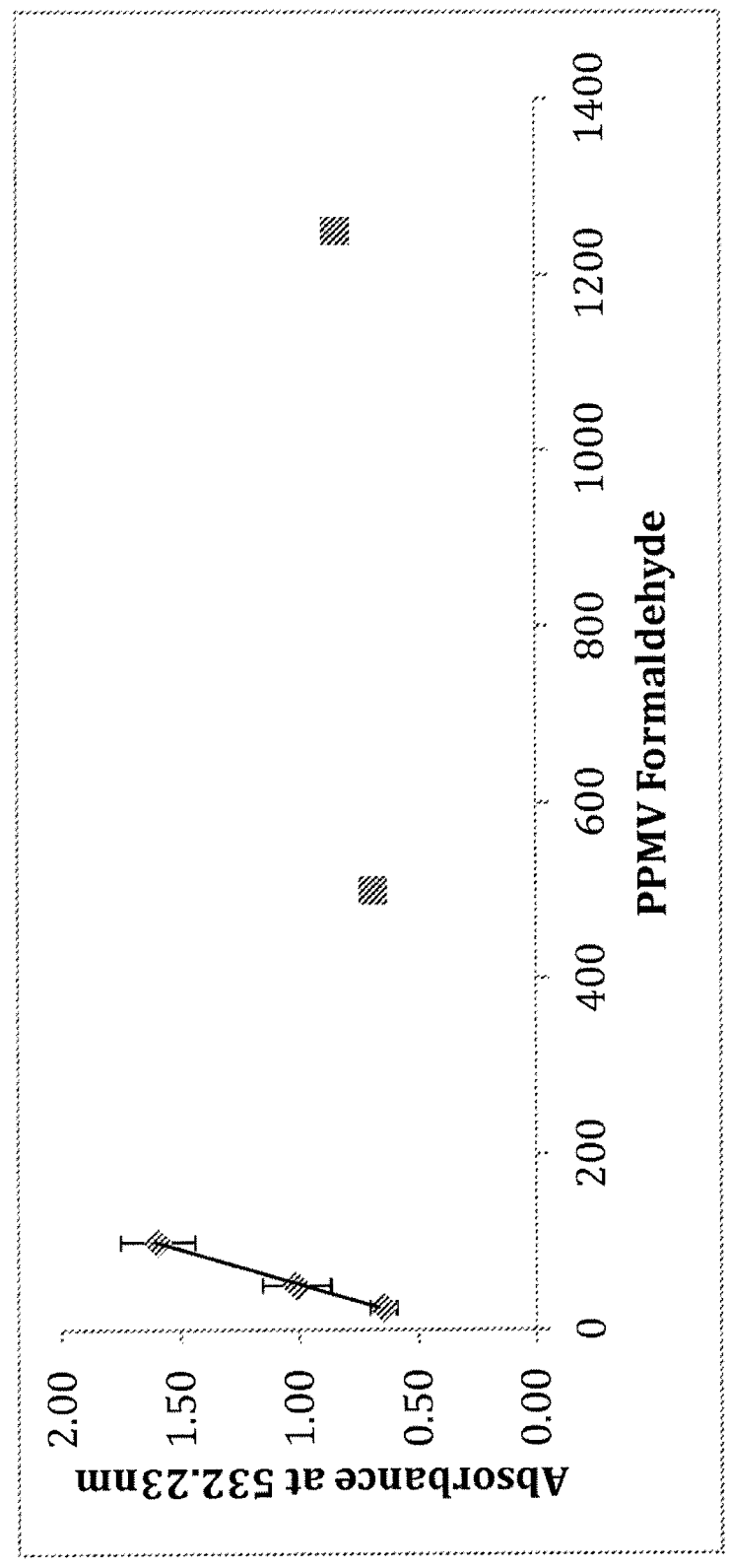
FIG. 7. Sets forth absorbance responses of resorcinol and additive-imbibed membranes at 532.23 nm after exposure to formaldehyde with concentration extension to 500 ppmv and 1250 ppmv to show the ability to shift the dynamic range.

In particular, a PSA (or PFSA) catalyst polymer membrane comprising an immobilized organic reagent capable of undergoing a synthetic reaction with an aldehyde, such as formaldehyde to produce a detectable color-shifted product is constructed as exemplified (see Example 6) herein. According to specific embodiments, the organic reagent is a dihydroxybenzene and in very specific embodiments the dihydroxybenzene comprises resorcinol. According to some embodiments, the immobilized organic acid is selected from the group consisting of tiglic acid, benzoic acid, vanillic acid, and ferulic acid; however it is understood that selection of the acid additive is guided by the desired pKa character, that is, the immobilized organic acid possesses a pKa greater than the pKa of the PSA polymer membrane. A person of ordinary skill in the art will be able to readily identify suitable acid additives given specific PSA polymer membrane properties. In very specific embodiments, the immobilized organic acid comprises tiglic acid. Optical sensors and portable optical sensing devices may be fabricated utilizing the inventive membranes and based on the inventive methods. FIGS. 5 and 6 and Examples 6 and 7 illustrate a specific PSA membrane formulation that enables detection of formaldehyde below 25 ppmv or above 100 ppmv at 100% relative humidity. The system was therefore very sensitive within a small dynamic range. As illustrated by FIG. 7, which sets for absorbanc responses at a different resorcinol concentration, the dynamic range for detection may be shifted.

The following Examples are set forth to illustrate particular embodiments, aspects and principles of the invention as described herein and should not be construed as limiting the scope thereof, as defined by the appended claims.

EXAMPLES

Example 1

The following Example illustrates that a PSA polymer membrane comprising immobilized resorcinol known in the art, reformulated to further comprise an additive comprising a small organic acid, retains its ability to catalyze a condensation reaction between the resorcinol and acetone present in the environment in a humid environment.

Nafion® membrane (The Fuel Cell Store, Nafion® 117, protonated, 0.007 in. thickness) is immersed in a 12 g/L solution of resorcinol (Acros Organics, 98%) in ethanol (Acros Organics, ACS spectroscopic grade, >95% purity) for 31 min. (See Ayyadurai, S. M.; Worrall, A. D.; Bernstein, J. A.; Angelopoulos, A. P. *Analytical Chemistry* 2010, 82, 6265 and Angelopoulos, A.; Berstein, J. A.; Kanter, D.; Ayyadurai, S.; University of Cincinnati: 2010 for a more detailed description of the previous preparation of PSA polymer membranes without an oil additive according to the instant disclosure. The content of both publications is incorporated herein by this reference.) The membranes are rinsed with deionized water and allowed to air dry. The membranes are then placed into a flask containing a concentration of vanillic acid or tiglic acid in 100% food grade mineral oil. As vanillic acid is not soluble in pure mineral oil, ethyl acetate is added to increase the solubility of the mixture. These acids are merely exemplary of organic acids which may be used to effectuate the desired retention of catalytic activity. Mineral oil is utilized to avoid loss of the resorcinol in the membrane during the organic acid uptake. The membranes soak in the solution for 1 hour to 24 hours depending on the rate of uptake observed and then excess oil solution is rinsed off and the membrane is allowed to air dry.

The membranes are then suspended in a sealed nitrogen purged flask with a known concentration of acetone (Acros Organics, ACS spectroscopic grade, 99% purity). For samples in the presence of water, an additional amount of water is added to the flask using a gas-tight syringe to reach the desired relative humidity (RH) for the experiment. Ambient conditions are measured prior to addition of water to account for the water content of the air in the flask which varied between 35% and 50% RH at 22° C. ensuring that the proper RH level is present in the flask when heated. The flask is then submersed in a water bath at 60° C. for 15 minutes. After the allotted equilibration time for the exposure, the membrane is removed and the signal response is observed ex-situ using an ultra-violet/visible spectrometer (Ocean Optics HR 2000+ CG-UV-NIR High Resolution Spectrometer). A bare Nafion membrane is used as the background for the spectroscopy software, SpectraSuite™.

It was observed that upon exposure to acetone at 100% relative humidity, the membranes changed color from a transparent light peach to a bright yellow-orange. This response confirms that the additive is mitigating water interference since a color change occurred in the presence of water. In contrast, a membrane without the additive shows negligible light absorption. The color change is explained by the drastic shift in absorption of the membrane at a wavelength of 400.69 nm, marking the reaction between resorcinol dye and the acetone.

Example 2

The following Example supports the hypothesis that the organic acid additive prevents PSA group de-protonation that occurs in the presence of water.

A water uptake study was performed to determine whether or not the oil imbibing solvent was preventing catalyst de-activation by preventing water from entering the membrane, or whether the mechanism involves the immobilized organic acid component. The uptake of water in a bare membrane was compared to the uptake of water in an oil additive soaked membrane using weight measurement. It was observed that there was no significant change in weight uptake between the membranes, confirming that the additive is not excluding water. This supports the mechanistic theory that the additive is preventing the sulfonic acid group de-protonation in the presence of water.

Example 3

The following Example illustrates that the oil-imbibed additive mitigates the interference with the PSA membrane catalytic capability known to occur in the presence of salt.

To further test this hypothesis, a cation exchange study was performed. The prepared resorcinol and oil additive soaked membranes were soaked in known concentrations of a 5 mM cesium (Cs) solution. The Cs cation is known to exchange with protons in the membrane. The exposure methodology for acetone was repeated with these membranes. Rather than the bright yellow-orange color response, the membranes changed to a dark magenta with the presence of water, acetone, and cesium. As shown in FIG. 3, at 5 mM concentration of cesium, the absorption of the membranes at the wavelength of 400.69 nm still experienced a drastic peak change, concluding the mitigation of salt interference with the incorporation of the oil additive. But as the concentration of cesium increased to 10 mM and 50 mM, the absorption level reading response declined. This indicates that the oil additive is mitigating cesium exchange up to a certain concentration.

Example 4

The following Example illustrates the correlation between measurement of acetone in exhaled human breath in accordance with embodiments of the invention, and simultaneously derived blood glucose concentration measured with a glucometer.

Breath samples were collected using nitrogen purged resealable 250 mL mylar bags with an attached mouthpiece. Each subject was instructed to take a deep breath, exhale out the first third of their breath and then blow the remaining air into two sample bags making sure that each is filled to capacity before going on to the next sample bag. This was done to ensure that the analysis sample contained the majority of the acetone present, which is found primarily in the last portion of exhalation. Blood glucose measurements were taken using a One Touch blood glucometer. Subjects were not restricted to fasting but had not eaten within an hour prior to testing.

1100 equivalent weight Nafion® membranes previously saturated with resorcinol in 12 g/L solution with ethanol were subsequently immersed in a solution of mineral oil and tiglic acid. The membranes were rinsed and dried. Samples of exhaled breath and blood form a patient were collected and analyzed simultaneously. The breath samples were tested by transferring the gas sample into a sealed nitrogen purged 250 mL round bottom flask containing a suspended treated membrane containing resorcinol and 50.0 g/L tiglic acid. The sample was then heated to 60° C. for 15 minutes and the absorbance was measured as detailed above. The results are set forth in FIG. 1. Light absorption by the sensing membrane is plotted on the y-axis and results from synthesis of a colored product, a flavan, due to the PSA-catalyzed condensation of acetone and resorcinol even in the presence of water. Light absorption is directly correlated to acetone concentration, as needed, using ex-situ calibration data (see FIG. 4). Blood glucose concentration was simultaneously measured in the blood samples using a glucometer and the corresponding reading was recorded on the x-axis. The equation on the chart is a linear fit to the patient data and the associated correlation coefficient for the linear regression is also shown (r2). Square data points represent patients with known diabetes (whether controlled or not). Data points at the low end of the blood glucose readings represent random control subjects without diabetes. The only restriction on the patients with respect to fasting is that required by the glucometer (minimum 2 hours after meals). Sample exhaled breath volumes in every case consisted of 500 ml collected after an initial 500 ml exhalation.

On the other hand, PSA catalyst membranes saturated with resorcinol according to the prior art, without the additional immersion oil imbibed additive, yielded negligible flavan synthesis and associated light absorption. In the absence of the immobilized organic acid and organic reagent, the sensing element became inoperative at human breath relative humidity levels due to the deactivation of the PSA functional groups. Ion-exchange of protons by cations such as $K^+$, $Ca^{++}$, and $Ce^{++}$ has been observed to yield similar de-activation.

Example 5

The following Example illustrates calibration of ambient acetone concentrations in the presence of 100% relative humidity using an optical sensor comprising a PSA polymer membrane comprising resorcinol and other exemplary immobilized organic acids.

The procedure of Example 2 is repeated by immobilizing Ferulic acid and Benzoic acid in the PSA membrane rather than tiglic acid. Benzoic acid gave substantially lower intensities, consistent with its higher proton affinity.

Example 6

The following Example demonstrates retention of catalytic activity of a PSA polymer membrane in accordance with embodiments of the invention in the condensation reaction between resorcinol and formaldehyde under humid conditions.

A PSA polymer membrane comprising immobilized resorcinol and immobilized organic acid is prepared in accordance with the method set forth in Example 1, above. The membrane is suspended in a 500 mL round bottom flask using Teflon tape and a piece of gold plated stainless steel. Working under a fume hood, 40 micro-liters of formaldehyde solution at varying concentrations of 25 ppmv, 50 ppmv, and 100 ppmv and 0.12 mL of water was injected into the flask and the flask was capped with a Teflon seal. These volumes are needed in order to reach a desired formaldehyde exposure level at a relative humidity of 100% in a 500 mL flask at 75° C. for 40 minutes to allow for the formaldehyde to completely volatize. The membrane is removed from the flask for measurement of the response.

Upon exposure to formaldehyde at 100% relative humidity, the membranes changed color from transparent light peach to scarlet red. This response confirms that the oil-imbibed additive is mitigating water interference since a color change occurred in the presence of water. In contrast, a membrane without the oil-imbibed additive showed negligible light absorption in conditions of 100% relative humidity. As the membranes are exposed to various concentrations of formaldehyde, there is a distinct increase in absorption over the visible light spectrum, which accounts for the color change that is produced, as seen in FIG. 5.

The visible spectrum absorption level peak is observed to be at a wavelength of 532.23 nm, marking the reaction between resorcinol and formaldehyde. Taking the absorbance levels at this wavelength, a linear correlation ($R^2=0.99$) between formaldehyde concentration and absorbance can be produced, as seen in FIG. 6.

Formaldehyde concentrations of 25 ppmv, 50 ppmv, and 100 ppmv were chosen because the concentrations greater than this saturated the visible spectrum and the concentrations less than this failed to generate a consistent peak. Although the specific membrane embodiment was unable to detect presence of formaldehyde below 25 ppmv or above 100 ppmv, the system was very sensitive within a small dynamic range (FIG. 6).

Example 7

The following Example demonstrates that changing resorcinol concentration in the PSA polymer membrane provides membranes with different formaldehyde detection range capability.

The resorcinol concentration in the resorcinol imbibing composition was decreased to 1g/L. Results of exposing this membrane to two formaldehyde concentrations substantially higher than those in FIG. 6 are shown in FIG. 7. The data in FIG. 6 is repeated in FIG. 7 to highlight the contrast in the dynamic range of the two membrane formulations.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. For example, any component or ingredient, etc., can be explicitly excluded. Applicants reserve the right to proviso out of the claims any specific component, category, or combination thereof, whether or not such is recited herein.

What is claimed:

1. An optical sensor for detecting a target compound in a humid environment, the optical sensor comprising:
   a perfluorosulfonic acid (PSA) polymer catalyst membrane comprising:
   (1) an immobilized organic acid selected from the group consisting of tiglic acid, benzoic acid, vanillic acid, and ferulic acid; and
   (2) an immobilized organic reagent, the immobilized organic reagent being capable of reacting with the target compound to produce a color shifted product;
   wherein exposure of the optical sensor to the target compound in the humid environment produces a detectable color shift on the optical sensor.

2. The optical sensor according to claim 1, wherein the immobilized organic reagent comprises a dihydroxybenzene.

3. The optical sensor according to claim 2, wherein the dihydroxybenzene comprises resorcinol.

4. The optical sensor according to claim 1, wherein the humid environment comprises exhaled human breath and the target compound comprises a volatile organic compound present in exhaled human breath.

5. The optical sensor according to claim 4, wherein the volatile organic compound comprises acetone and the immobilized organic acid is tiglic acid.

6. A portable optical sensing device for detection of acetone in exhaled human breath, the portable optical sensing device comprising the optical sensor according to claim 5.

7. The optical sensor according to claim 1, wherein the humid environment comprises fuel cell effluent and the target compound comprises formaldehyde.

8. A portable optical sensing device for detection of formaldehyde in fuel cell effluent comprising the optical sensor according to claim 7.

9. The optical sensor according to claim 1, wherein the humid environment comprises a relative humidity of up to 100%.

10. The optical sensor according to claim 1, wherein the immobilized organic acid has a pKa of at least 4.2.

* * * * *